(12) United States Patent
Brause

(10) Patent No.: US 12,295,606 B2
(45) Date of Patent: May 13, 2025

(54) ENGAGEMENT FEATURES AND METHODS FOR ATTACHING A DRIVE ROD TO A KNIFE BLADE IN AN ARTICULATING SURGICAL INSTRUMENT

(71) Applicant: Covidien LP, Mansfield, MA (US)

(72) Inventor: David D. Brause, Longmont, CO (US)

(73) Assignee: Covidien LP, Mansfield, MA (US)

( * ) Notice: Subject to any disclaimer, the term of this patent is extended or adjusted under 35 U.S.C. 154(b) by 81 days.

(21) Appl. No.: 17/982,124

(22) Filed: Nov. 7, 2022

(65) Prior Publication Data

US 2023/0055798 A1     Feb. 23, 2023

Related U.S. Application Data

(63) Continuation of application No. 16/832,782, filed on Mar. 27, 2020, now Pat. No. 11,490,916.
(Continued)

(51) Int. Cl.
    *A61B 17/295*     (2006.01)
    *A61B 17/3211*     (2006.01)
(Continued)

(52) U.S. Cl.
CPC ........ *A61B 17/295* (2013.01); *A61B 17/3211* (2013.01); *A61B 2017/00734* (2013.01); *A61B 2017/00867* (2013.01); *A61B 17/320068* (2013.01); *A61B 2018/00077* (2013.01); *A61B 2018/00589* (2013.01); *A61B 2018/00595* (2013.01); *A61B 2018/0063* (2013.01);
(Continued)

(58) Field of Classification Search
CPC .. A61B 2017/07285; A61B 2018/1452; A61B 17/3211; A61B 17/068–07292; A61B 17/28–17/295; A61B 17/115–2017/1157; A61B 2018/1455; A61B 2018/1457
USPC .................................................. 606/166–185
See application file for complete search history.

(56) References Cited

U.S. PATENT DOCUMENTS

| | | | | |
|---|---|---|---|---|
| 2,061 | A * | 4/1841 | Van Osdel | A61B 5/150442 |
| | | | | 30/272.1 |
| 518,600 | A * | 4/1894 | Hallman | A61B 17/320725 |
| | | | | 606/170 |

(Continued)

FOREIGN PATENT DOCUMENTS

| | | |
|---|---|---|
| CN | 201299462 Y | 9/2009 |
| DE | 2415263 A1 | 10/1975 |

(Continued)

OTHER PUBLICATIONS

Heniford et al. "Initial Research and Clinical Results with an Electrothermal Bipolar Vessel Sealer" Oct. 1999.
(Continued)

*Primary Examiner* — Kathleen S Holwerda

(57) ABSTRACT

A knife assembly for use with a surgical instrument includes a knife having proximal and distal ends, the proximal end including an aperture defined therein having a series of spaced apart fins extending thereacross. A knife drive rod is included and is configured to operably engage the fins to secure the knife drive rod to the knife. A retention mechanism is operably disposed at a distal end of the knife drive rod and is configured to secure the knife drive rod in engagement between the fins.

10 Claims, 11 Drawing Sheets

Related U.S. Application Data

(60) Provisional application No. 62/825,882, filed on Mar. 29, 2019.

(51) Int. Cl.

| | |
|---|---|
| A61B 17/00 | (2006.01) |
| A61B 17/32 | (2006.01) |
| A61B 18/00 | (2006.01) |
| A61B 18/08 | (2006.01) |
| A61B 18/14 | (2006.01) |
| A61B 18/18 | (2006.01) |
| A61B 34/35 | (2016.01) |

(52) U.S. Cl.
CPC ......... *A61B 18/085* (2013.01); *A61B 18/1445* (2013.01); *A61B 2018/1455* (2013.01); *A61B 2018/1807* (2013.01); *A61B 2018/1861* (2013.01); *A61B 34/35* (2016.02)

(56) References Cited

U.S. PATENT DOCUMENTS

| | | | |
|---|---|---|---|
| 2,730,101 A * | 1/1956 | Hoffman | A61B 17/320725 606/108 |
| D249,549 S | 9/1978 | Pike | |
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| 5,391,166 A | 2/1995 | Eggers | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| 5,904,699 A | 5/1999 | Schwemberger et al. | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 9,084,608 B2 | 7/2015 | Larson et al. | |
| 9,211,657 B2 | 12/2015 | Ackley et al. | |
| 11,490,916 B2 | 11/2022 | Brause | |
| 2007/0016237 A1 | 1/2007 | Smith | |
| 2008/0077146 A1 * | 3/2008 | Pernsteiner | A61B 17/3213 606/172 |
| 2010/0081875 A1 | 4/2010 | Fowler | |
| 2012/0083783 A1 | 4/2012 | Davison | |
| 2012/0116416 A1 | 5/2012 | Neff et al. | |
| 2014/0221995 A1 | 8/2014 | Guerra et al. | |
| 2014/0221999 A1 | 8/2014 | Cunningham et al. | |
| 2014/0222055 A1 | 8/2014 | Smith | |
| 2014/0228842 A1 | 8/2014 | Dycus et al. | |
| 2014/0230243 A1 | 8/2014 | Roy et al. | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1 | 9/2014 | Hixson et al. | |
| 2014/0250686 A1 | 9/2014 | Hempstead et al. | |
| 2014/0257274 A1 | 9/2014 | McCullough, Jr. et al. | |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0276803 A1 | 9/2014 | Hart | |
| 2014/0284313 A1 | 9/2014 | Allen, IV et al. | |
| 2014/0288549 A1 | 9/2014 | McKenna et al. | |
| 2014/0288553 A1 | 9/2014 | Johnson et al. | |
| 2014/0330308 A1 | 11/2014 | Hart et al. | |
| 2014/0336635 A1 | 11/2014 | Hart et al. | |
| 2014/0353188 A1 | 12/2014 | Reschke et al. | |
| 2014/0364851 A1 | 12/2014 | Batross | |
| 2015/0018816 A1 | 1/2015 | Latimer | |
| 2015/0025528 A1 | 1/2015 | Arts | |
| 2015/0032106 A1 | 1/2015 | Rachlin | |
| 2015/0051598 A1 | 2/2015 | Orszulak et al. | |
| 2015/0051640 A1 | 2/2015 | Twomey et al. | |
| 2015/0066026 A1 | 3/2015 | Hart et al. | |
| 2015/0080880 A1 | 3/2015 | Sartor et al. | |
| 2015/0080889 A1 | 3/2015 | Cunningham et al. | |
| 2015/0082928 A1 | 3/2015 | Kappus et al. | |
| 2015/0088122 A1 | 3/2015 | Jensen | |
| 2015/0088126 A1 | 3/2015 | Duffin et al. | |
| 2015/0088128 A1 | 3/2015 | Couture | |
| 2015/0094714 A1 | 4/2015 | Lee et al. | |

FOREIGN PATENT DOCUMENTS

| | | |
|---|---|---|
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 3627221 A1 | 2/1988 |
| DE | 8712328 U1 | 2/1988 |
| DE | 4303882 A1 | 8/1994 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |

(56) References Cited

FOREIGN PATENT DOCUMENTS

| | | |
|---|---|---|
| DE | 20121161 U1 | 4/2002 |
| DE | 1004537502 | 10/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |
| DE | 102008018406 B3 | 7/2009 |
| EP | 1159926 A2 | 12/2001 |
| EP | 1281878 A1 | 2/2003 |
| JP | 61501068 | 9/1984 |
| JP | 1024051 | 1/1989 |
| JP | 6502328 | 3/1992 |
| JP | 55106 | 1/1993 |
| JP | H0540112 A | 2/1993 |
| JP | 6121797 | 5/1994 |
| JP | 6285078 | 10/1994 |
| JP | H06343644 A | 12/1994 |
| JP | H07265328 A | 10/1995 |
| JP | 08056955 | 3/1996 |
| JP | 08252263 | 10/1996 |
| JP | 8289895 | 11/1996 |
| JP | 8317934 | 12/1996 |
| JP | 8317936 | 12/1996 |
| JP | 09000538 | 1/1997 |
| JP | H0910223 A | 1/1997 |
| JP | 9122138 | 5/1997 |
| JP | 0010000195 | 1/1998 |
| JP | 10155798 | 6/1998 |
| JP | 1147149 | 2/1999 |
| JP | 1147150 | 2/1999 |
| JP | 11070124 | 3/1999 |
| JP | 11169381 | 6/1999 |
| JP | 11192238 | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2001003400 | 11/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| JP | 6511401 | 5/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A3 | 4/2006 |
| WO | 2008040483 A1 | 4/2008 |
| WO | 2011018154 A1 | 2/2011 |
| WO | 2016025132 A1 | 2/2016 |

OTHER PUBLICATIONS

Michael Choti, "Abdominoperineal Resection with the LigaSure Vessel Sealing System and LigaSure Atlas 20 cm Open Instrument" Innovations That Work, Jun. 2003.

Chung et al., "Clinical Experience of Sutureless Closed Hemorrhoidectomy with LigaSure" Diseases of the Colon & Rectum vol. 46, No. Jan. 1, 2003.

Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.

Peterson et al., "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000, 6 pages.

Johnson et al. "Evaluation of a Bipolar Electrothermal Vessel Sealing Device in Hemorrhoidectomy" Sales/Product Literature; Jan. 2004, 1 page.

E. David Crawford, "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al. "Extended Left Hemicolectomy Using the LigaSure Vessel Sealing System" Innovations That Work; Sep. 1999.

Kennedy et al., "High-burst-strength, feedback-controlled bipolar vessel sealing" Surgical Endoscopy (1998) 12:376-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females". Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal Hysterectomy" Obstetrics & Gynecology, vol. 102, No. 1, Jul. 2003.
Reducing Needlestick Injuries in the Operating Room Sales/Product Literature 2001_ (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. Jul. 1, 2001 pp. 21-24.
Levy et al., "Update on Hysterectomy—New Technologies and Techniques" OBG Management, Feb. 2003. (15 pages.).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery {2001} 71 .9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C . . . (1 Page).
E. David Crawford, "Use of a Novel Vessel Sealing Technology in Management of the Dorsal Veinous Complex" Sales! Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue" MICCAI 2005; LNCS 3750 pp. 624-632 Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler (abandoned).
U.S. Appl. No. 09/177,950, filed Oct. 23, 1998; inventor: Randel A. Frazier (abandoned).
U.S. Appl. No. 09/387,883, filed Sep. 1, 1999; inventor: Dale F. Schmaltz (abandoned).
U.S. Appl. No. 09/591,328, filed Jun. 9, 2000; inventor: Thomas P. Ryan (abandoned).
U.S. Appl. No. 12/336,970, filed Dec. 17, 2008; inventor: Paul R. Sremeich (abandoned).
U.S. Appl. No. 14/065,644, filed Oct. 29, 2013; inventor: Reschke (abandoned).

\* cited by examiner

ENGAGEMENT FEATURES AND METHODS FOR ATTACHING A DRIVE ROD TO A KNIFE BLADE IN AN ARTICULATING SURGICAL INSTRUMENT

CROSS REFERENCE TO RELATED APPLICATIONS

This application is a continuation of U.S. patent application Ser. No. 16/832,782, filed on Mar. 27, 2020, which claims the benefit of and priority to U.S. Provisional Patent Application No. 62/825,882, filed on Mar. 29, 2019, the entire contents of each of which is incorporated by reference herein.

BACKGROUND

Technical Field

The present disclosure relates surgical instruments, and more particularly, to various engagement features and methods for attaching a drive rod to a knife blade to facilitate actuation thereof.

Background of Related Art

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife or cutting member utilized to effectively sever the treated tissue.

Many electrosurgical forceps include various actuators to orient the jaw members for tissue treatment. For example, many forceps include rotational wheels (or the like) disposed in proximity to a surgeon's hands to enable the surgeon to selectively rotate the jaw members as needed during an operation. A trigger (or similar) may be disposed on the forceps housing to allow a surgeon to selectively deploy a knife or cutting element as needed during surgery. Other actuators include articulating mechanisms disposed in proximity to the surgeon's hands to allow the surgeon to selectively articulate (e.g., pitch and yaw) the jaw members as needed during surgery.

With particular respect to articulating forceps that include a deployable knife, one important feature of these types of forceps is the knife drive rod which typically needs to be both sufficiently flexible to allow articulation of the jaw members while also being strong enough to advance and retract a knife blade through tissue.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

In accordance with aspects of the present disclosure, a knife assembly for use with a surgical instrument is provided and includes a knife having proximal and distal ends. The proximal end of the knife includes an aperture defined therein having a series of spaced apart fins extending thereacross. A knife drive rod is configured to operably engage the fins to secure the knife drive rod to the knife, and a retention mechanism is operably disposed at a distal end of the knife drive rod and is configured to secure the knife drive rod in engagement between the fins.

In aspects according to the present disclosure, the retention mechanism is a cap or any other type of enlarged area at a distal end thereof, e.g., forged head, molten bubble, additional material via welding, crimping, swaging, etc. In other aspects according to the present disclosure, the retention mechanism includes the knife having a second aperture defined therein configured to receive a bent end of the knife drive rod.

In aspects according to the present disclosure, one or more of the fins includes a recess defined therein configured to receive at least a portion of an outer periphery of the knife drive rod. In still other aspects according to the present disclosure, the knife drive rod is configured to engage the fins in a weave-like manner from a proximal end of the aperture to a distal end of the aperture.

In accordance with additional aspects of the present disclosure, a knife assembly for use with a surgical instrument is provided and includes a knife having proximal and distal ends, the proximal end including an aperture defined therein. A knife drive rod includes a tube operably engaged to a distal end thereof. The tube is configured to operably engage the aperture to lock the knife drive rod in engagement with the knife. In aspects according to the present disclosure, a weld operably engages the tube to the knife. In other aspects according to the present disclosure, the distal end of the knife drive rod threadably engages the tube. In still other aspects according to the present disclosure, the knife and the tube are made from similar metals to increase the strength of the weld.

In yet other aspects according to the present disclosure, the tube is dimensioned to seat within the aperture and, once seated, provides a first mechanical engagement between the tube and the knife, and a weld provides a second mechanical engagement between the tube and the knife. Other methods of mechanical engagement are contemplated, e.g., crimping and swaging. In still other aspects according to the present disclosure, the knife includes a second aperture defined therein configured to receive a bent end of the knife drive rod to provide a second mechanical engagement between the knife and the knife drive rod. In other aspects according to the present disclosure, the second aperture is a slot and the bent end of the knife includes a locking feature to secure the distal end of the knife drive rod within the slot once engaged therein. In yet other aspects according to the present disclosure, the locking feature is a twist lock, a tab lock, a button snap, a crimp, or a rivet.

In accordance with additional aspects of the present disclosure, a knife assembly for use with a surgical instrument includes a knife having proximal and distal ends. The proximal end includes an aperture defined therein including a pair of tubes operably engaged thereto. A knife drive rod is configured to operably engage the pair of tubes disposed within the aperture. A knife tube is operably engaged to the knife drive rod between the pair of tubes. The knife tube is dimensioned larger than the pair of tubes to lock the knife drive rod within the pair of tubes and in operable engagement with the knife.

In aspects according to the present disclosure, a weld secures each tube of the pair of tubes to the knife, and a knife weld secures the knife tube to the knife drive rod. In yet other aspects according to the present disclosure, the pair of tubes and the knife are made from similar metals, and the knife tube and the knife drive rod are made from similar materials to increase the strength of the welds.

In accordance with additional aspects of the present disclosure, a knife assembly for use with a surgical instrument includes a knife having proximal and distal ends. The proximal end includes an aperture defined therein having one or more capture tabs disposed therein. A tube is configured to operably engage the one or more capture tabs disposed within the aperture. A knife drive rod is configured to operably engage the tube disposed within the aperture.

In aspects according to the present disclosure, the knife drive rod threadably engages the tube. In other aspects according to the present disclosure, the tube is dimensioned to seat within the aperture and, once seated, provides a first mechanical engagement between the tube and the knife, and a weld provides a second mechanical engagement between the tube and the knife. In aspects according to the present disclosure, the aperture includes a pair of opposing capture tabs each configured to engage an end of the tube.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and.

DETAILED DESCRIPTION

Figure 1A:
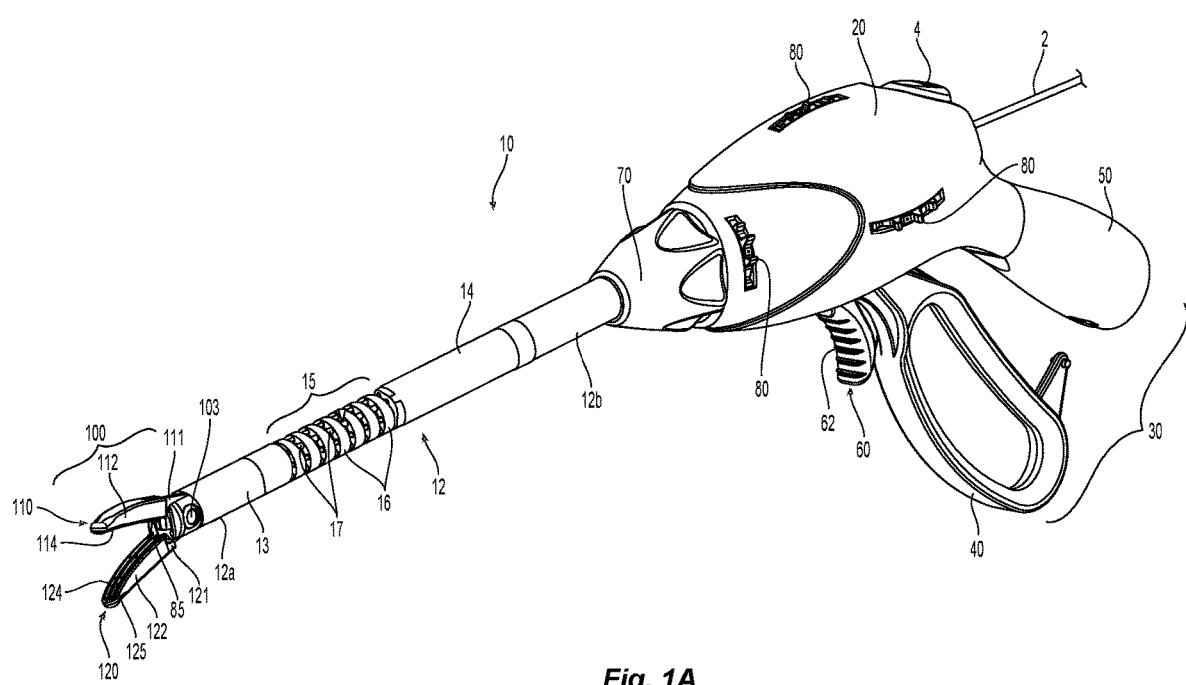
FIG. 1A is a perspective view of endoscopic surgical forceps exemplifying the aspects and features of the present disclosure, wherein the shaft of the endoscopic surgical forceps is disposed in a non-articulated position and wherein the jaw members of the endoscopic surgical forceps are disposed in a spaced-apart position.
Figure 1B:
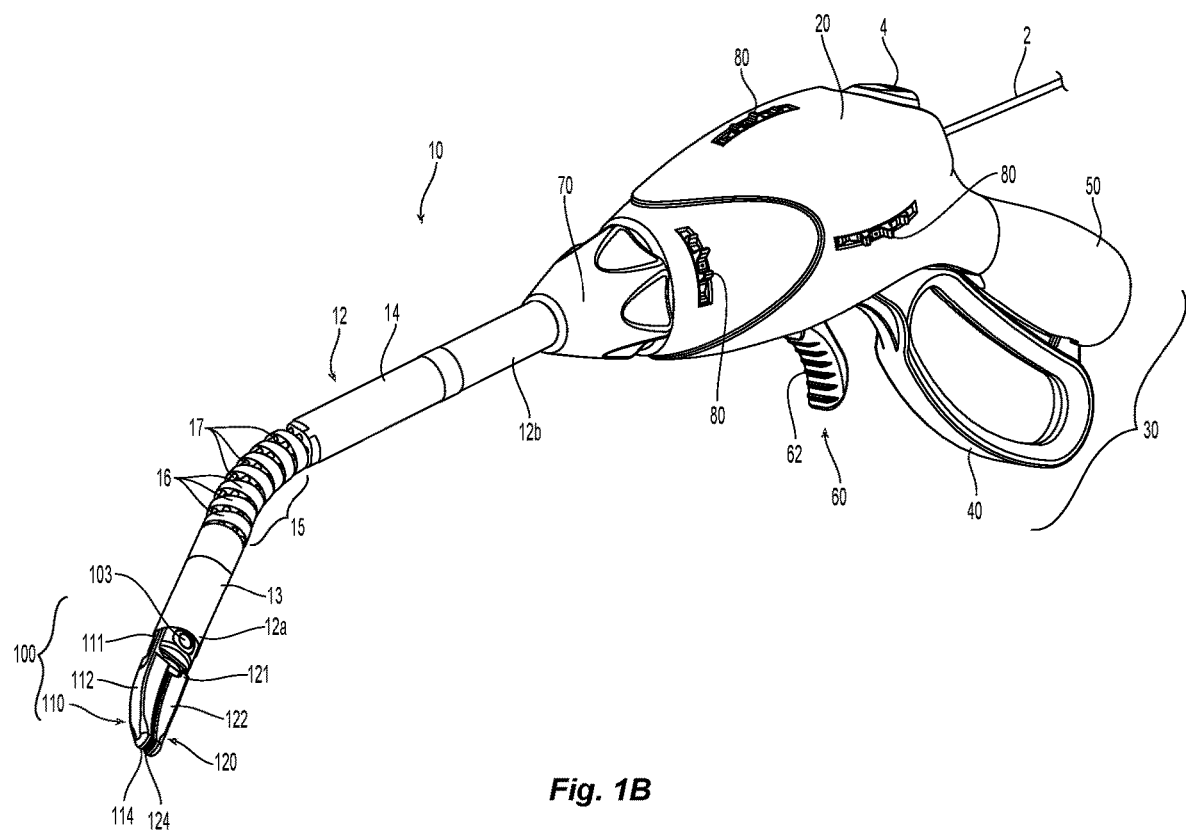
FIG. 1B is a perspective view of the endoscopic surgical forceps of FIG. 1A, wherein the shaft of the endoscopic surgical forceps is disposed in an articulated position and wherein the jaw members of the endoscopic surgical forceps are disposed in an approximated position.

Referring generally to FIGS. 1A and 1B, an endoscopic surgical forceps exemplifying the aspects and features of the present disclosure is shown generally identified by reference numeral 10. For the purposes herein, endoscopic surgical forceps 10 is generally described. Aspects and features of endoscopic surgical forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, a plurality of articulation actuators 80, an activation switch 4, and an end effector assembly 100. Forceps 10 further includes a shaft 12 having a distal end 12a configured to mechanically engage end effector assembly 100 and a proximal end 12b that mechanically engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating plates 114, 124 of jaw members 110, 120, respectively, of end effector assembly 100. Activation switch 4 is coupled to tissue-treating plates 114, 124 and the source of energy for selectively activating the supply of energy to jaw members 110, 120 for treating, e.g., cauterizing, coagulating/desiccating, and/or sealing, tissue.

Shaft 12 of forceps 10 defines a distal segment 13 positioned towards distal end 12a thereof, a proximal segment 14 positioned towards proximal end 12b thereof, and an articulating section 15 disposed between the distal and proximal segments 13, 14, respectively. Articulating section 15 includes a plurality of articulating links 16 having a plurality of articulation cables 17 extending therethrough. Each cable 17 is operably engaged at a distal end thereof to distal segment 13 and at a proximal end thereof to one of the articulation actuators 80 to enable articulation of distal segment 13 and, thus, end effector assembly 100, relative to proximal segment 14 upon actuation of one or more of articulation actuators 80. Rotating assembly 70 operably couples shaft 12 to housing 20 to enable selective rotation of shaft 12 and, thus, end effector assembly 100, relative to housing 20.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position (FIG. 1A) and an approximated position (FIG. 1B) to grasp tissue between jaw members 110, 120. As shown in FIG. 1A, movable handle 40 is initially spaced-apart from fixed handle 50 and, correspondingly, jaw members 110, 120 of end effector assembly 100 are disposed in the spaced-apart position. Movable handle 40 is compressible from this initial position to a compressed position corresponding to the approximated position of jaw members 110, 120 (FIG. 1B).

Trigger assembly 60 includes a trigger 62 coupled to housing 20 and movable relative thereto between an un-actuated position and an actuated position. Trigger 62 is operably coupled to a cutting mechanism 85, various embodiments of which are detailed below, to actuate the cutting mechanism 85 to cut tissue grasped between jaw members 110, 120 of end effector assembly 100 upon actuation of trigger 62. As an alternative to a pivoting trigger 62, a slide trigger, push-button, toggle switch, or other suitable actuator may be provided.

End effector assembly 100, as noted above, includes first and second jaw members 110, 120. Each jaw member 110, 120 includes a proximal flange portion 111, 121, an outer insulative jaw housing 112, 122 disposed about the distal portion (not explicitly shown) of each jaw member 110, 120, and a tissue-treating plate 114, 124, respectively. Proximal flange portions 111, 121 are pivotably coupled to one another about pivot 103 for moving jaw members 110, 120 between the spaced-apart and approximated positions, although other suitable mechanisms for pivoting jaw members 110, 120 relative to one another are also contemplated. The distal portions (not explicitly shown) of the jaw members 110, 120 are configured to support jaw housings 112, 122, and tissue-treating plates 114, 124, respectively, thereon.

Outer insulative jaw housings 112, 122 of jaw members 110, 120 support and retain tissue-treating plates 114, 124 on respective jaw members 110, 120 in opposed relation relative to one another. Tissue-treating plates 114, 124 are formed from an electrically conductive material, e.g., for conducting electrical energy therebetween for treating tissue, although tissue-treating plates 114, 124 may alternatively be configured to conduct any suitable energy, e.g., thermal, microwave, light, ultrasonic, etc., through tissue grasped therebetween for energy-based tissue treatment. As mentioned above, tissue-treating plates 114, 124 are coupled to activation switch 4 and the source of energy (not shown), e.g., via the wires (not shown) extending from cable 2 through forceps 10, such that energy may be selectively supplied to tissue-treating plate 114 and/or tissue-treating plate 124 and conducted therebetween and through tissue disposed between jaw members 110, 120 to treat tissue.

One or both of jaw members 110, 120 may further define a longitudinally-extending channel 125 (only the channel 125 of jaw member 120 is shown) for allowing reciprocation of the cutting mechanism 85 upon actuation of trigger 62. Actuation of the trigger 62 reciprocates a knife drive bar, e.g., knife drive rod 280 of FIG. 2B, operably coupled to the cutting mechanism, e.g., knife 285. As explained below, the term "rod" is generally utilized herein but is meant to denote any type of drive member or element. Together and as used herein, the knife, e.g., knife 285 and knife drive bar, e.g., knife drive rod 280, form a knife assembly 250. Knife drive rod 280 is made from a flexible material of sufficient strength to allow the knife drive rod 280 to both push and pull the knife 285 through tissue disposed between jaw members 110, 120. Moreover, the flexibility of the knife drive rod 280 allows the knife drive rod 280 to flex as needed during articulation of the jaw members 110, 120. The knife drive rod 280 may be made from a variety of flexible materials such as Nitinol that exhibit the necessary strength and flexibility to allow smooth translation of the knife drive rod 280 through one or more articulating joints of articulating section 15, e.g., Stainless Steel, High Carbon Steel, Iconel, Monel, Nimonic, Nitronic, Hastelloy (Nickel-based alloys other than Nitonol), Elgiloy (Cobalt-Nickel), Brass, Phosphor Brass, Beryllium Copper, Chrome-Vanadium, Chrome Silicone, Titanium and Braided Cable made of steel or Tungsten.

The knife drive rod 280 generally refers to a drive member that may be in the shape of a rod, cable, braided cable, tube, piece of sheet metal or plastic, screw and the like. It is envisioned that the term "rod" covers all of these and other commonly known types of drive members made from a variety of different materials so long as it is strong enough, durable enough and/or stiff enough to advance and retract the knife 285.

Knife 285 is typically made from a stronger, harder, stiffer and/or more durable material, e.g., stainless steel, to allow the knife 285 to easily translate through tissue on a repeated basis. Other materials are also contemplated such as Stainless Steel or High Carbon Steel, Tool Steel, High Speed Steel, Chrome Steel, Tungsten Carbide, Titanium, Vanadium Alloys, Ceramic or Glass and/or Plastic.

Since it is often difficult to assure a consistent and strong weld between two dissimilar metals, i.e., utilizing a flexible first material, e.g., Nitinol, for the knife drive rod 280 with a second stronger material for the knife 285, e.g., stainless steel, various welding and mechanical capture techniques are described below with respect to FIGS. 2A-10.

Figure 2A:
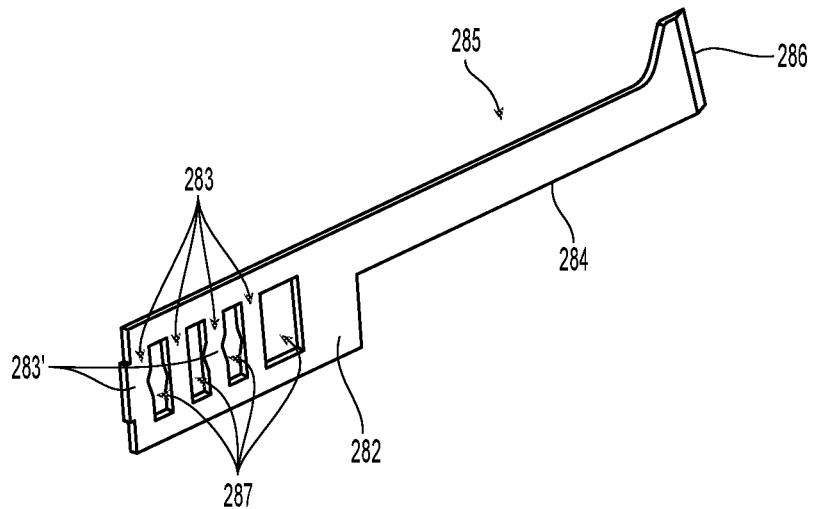
FIGS. 2A and 2B are enlarged schematic views of one embodiment of an engagement feature for coupling a knife blade to a knife drive rod exemplifying the aspects and features of the present disclosure.
Figure 2B:
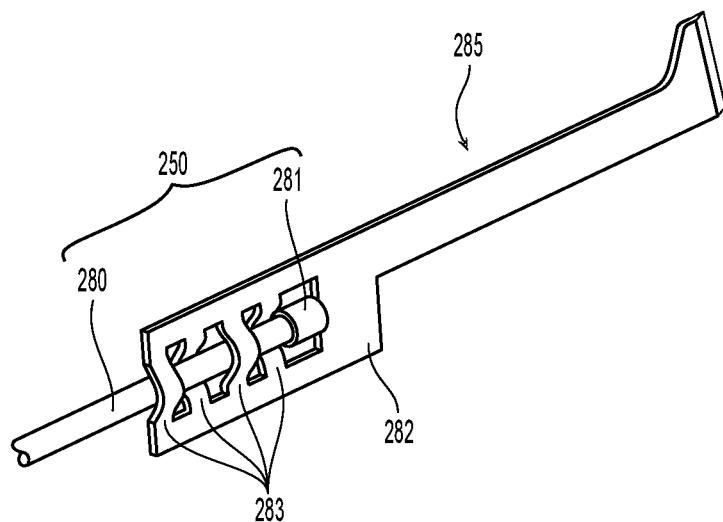

FIGS. 2A and 2B show one embodiment of a knife 285 for engagement to a knife drive rod 280. More particularly, knife 285 includes a knife body 284 having a distal end 286 and a proximal end 282, the distal end 286 including a sharpened edge for cutting tissue and the proximal end 282 including an aperture 287 defined therein for capturing the knife drive rod 280. Together the knife 285 and knife drive rod 280 form a knife assembly 250. A series of fins 283 are etched from the proximal end 282 into the aperture 287 that include one or more recessed portions 283' defined therein configured to partially receive the outer periphery of the knife drive rod 280 to mechanically capture the knife drive rod 280 on opposing sides along the length thereof. During assembly, the knife drive rod 280 is weaved through the various fins 283 to engage the recesses 283' and secure the knife drive rod 280 to the knife 285. Weaving the knife drive rod 280 through the fins 283 provides lateral stability to the knife 285 and knife drive rod 280 during use. Once the knife drive rod 280 is weaved through the fins 283, a retention mechanism, e.g., a cap 281, is secured (e.g., welded, crimped, etc.) to the end of the knife drive rod 280 to lock the knife drive rod 280 in place within aperture 287 of knife 285. Other types of enlarged areas may be utilized as a retention mechanism, e.g., forged head, molten bubble, additional material via welding, crimping, swaging, etc. The dimensions of the cap 281 are sized greater than the dimensions of the recesses 283' to prevent slippage of the mechanical connection during use. The knife 285 may be made from stainless steel, e.g., surgical stainless steel (316 SS) or other surgical metal, and the knife drive rod 280 may be made from Nitinol or other flexible metal or a metal hybrid (Nitinol inner rod and helical hollow strand HHS outer casing).

Figure 3A:
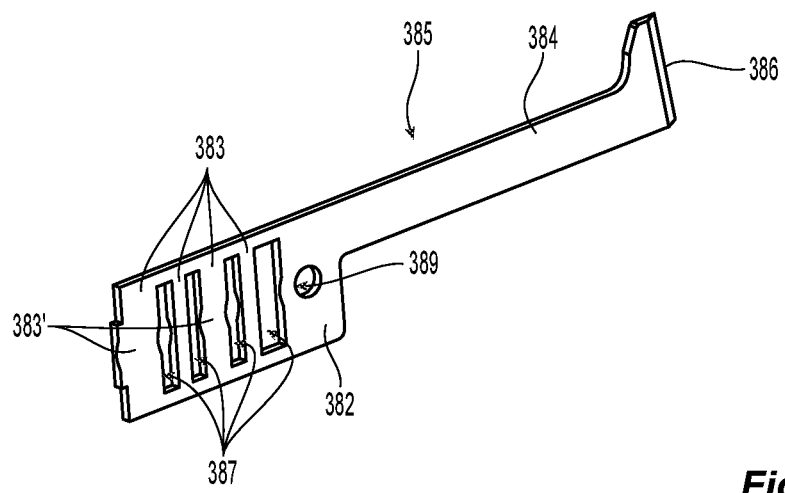
FIGS. 3A, 3B and 3C are enlarged schematic views of another embodiment of an engagement feature for coupling a knife blade to a knife drive rod exemplifying the aspects and features of the present disclosure.
Figure 3B:
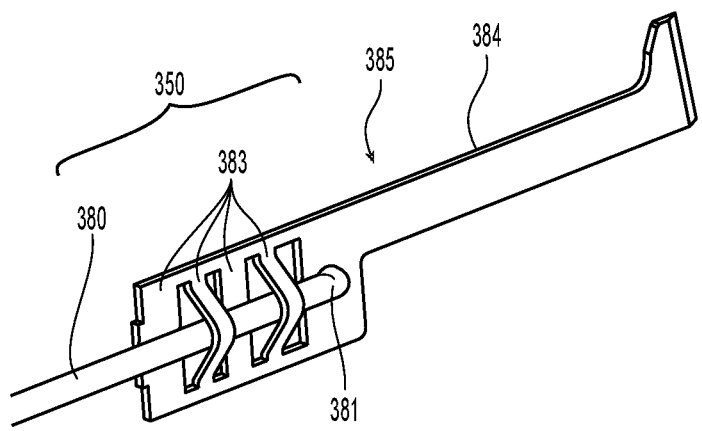
Figure 3C:
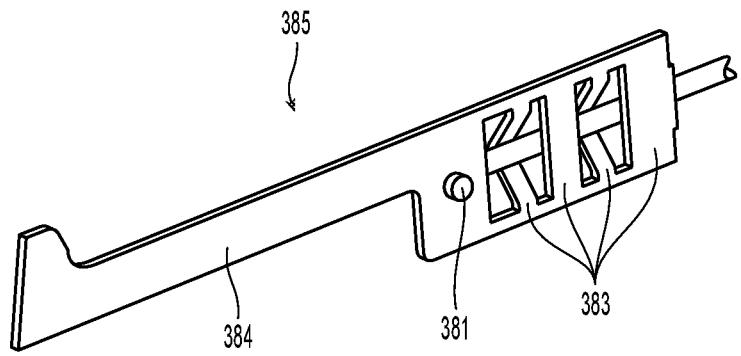

FIGS. 3A-3C show another embodiment of a knife 385 for engagement to a knife drive rod 380. More particularly, knife 385 includes a knife body 384 having a distal end 386 and a proximal end 382, the distal end 386 including a sharpened edge for cutting tissue and the proximal end 382 including an aperture 387 defined therein for capturing the knife drive rod 380. Together the knife 385 and knife drive rod 380 form a knife assembly 350. A series of fins 383 are etched from the proximal end 382 into the aperture 387 that include one or more recessed portions 383' defined therein configured to partially receive the outer periphery of the knife drive rod 380 to mechanically capture the knife drive rod 380 on opposing sides along the length thereof.

During assembly, the knife drive rod 380 is weaved through the various fins 383 to engage the recesses 383' and secure the knife drive rod 380 to the knife 385. As mentioned above, weaving the knife drive rod 380 through the fins 383 provides lateral stability to the knife 385 and knife drive rod 380 during use. Once the knife drive rod 380 is weaved through the fins 383, a retention mechanism, e.g., a bent end 381 disposed at the distal end of the knife drive rod 380, is secured within a corresponding aperture 389 defined within the proximal end 382 of the knife body 384 (FIG. 3B) to lock the knife drive rod 380 in place within aperture 389 of knife body 384 (FIG. 3C).

Figure 4A:
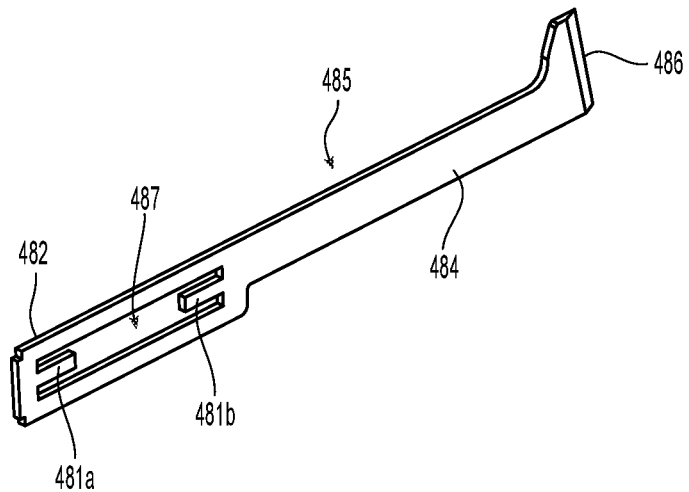
FIGS. 4A and 4B are enlarged schematic views of another embodiment of an engagement feature for coupling a knife blade to a knife drive rod exemplifying the aspects and features of the present disclosure.
Figure 4B:
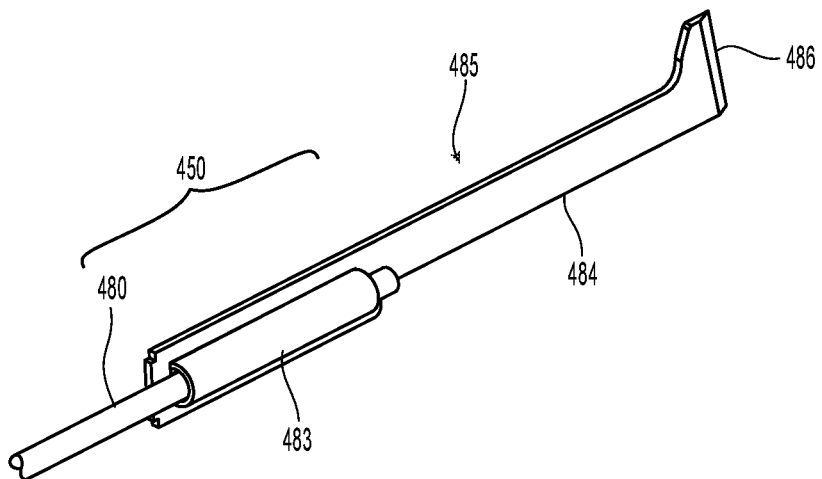

FIGS. 4A and 4B show another embodiment of a knife 485 for engagement to a knife drive rod 480. More particularly, knife 485 includes a knife body 484 having a distal end 486 and a proximal end 482, the distal end 486 including a sharpened edge for cutting tissue and the proximal end 482 including an aperture 487 defined therein for capturing the knife drive rod 480. Together the knife 485 and knife drive rod 480 form a knife assembly 450. A pair of opposing capture tabs 481a and 481b are etched from the proximal end 482 into the aperture 487 and are configured to capture and secure a tube 483 therebetween. The inner periphery of the tube 483 is configured to engage, e.g., threadably engage, the knife drive rod 480. During assembly, the tube 483 and the knife drive rod 480 may be spot-welded or crimped after engagement within the tube 483 to provide additional engagement of the knife drive rod 480 therein.

Since the knife drive rod 480 needs to be flexible to accommodate articulation of the jaw members 110, 120, and the knife body 484 needs to be sufficiently strong to cut through tissue on a repeated basis, the knife drive rod 480 and the knife body 484 are typically made from dissimilar materials and any such weld or bond may be weaker than desired. Thus, additional mechanical engagement between the two elements, e.g., the knife drive rod 480 and knife body 484, is needed to prevent mechanical failure. Tube 483 may be made from any type of metal, e.g., stainless steel, that will provide a secure weld to knife body 484. In embodiments, the knife body 484 and the tube 483 are made from the same material, e.g., stainless steel, to assure a good weld.

By providing a strong mechanical connection between the knife drive rod 480 and the tube 483 and a strong mechanical connection between the tube 483 and the knife body 484, the chances of mechanical failure are greatly reduced.

Figure 5A:
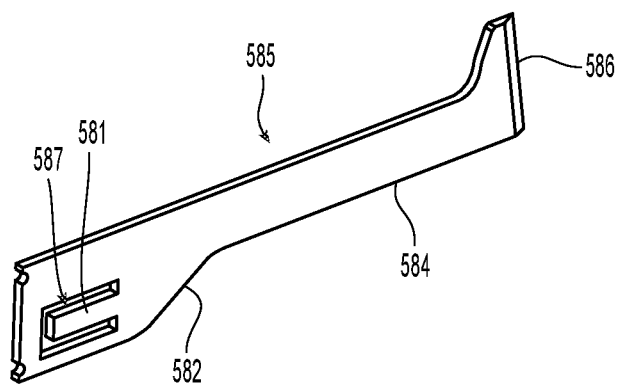
FIGS. 5A, 5B and 5C are enlarged schematic views of another embodiment of an engagement feature for coupling a knife blade to a knife drive rod exemplifying the aspects and features of the present disclosure.
Figure 5B:
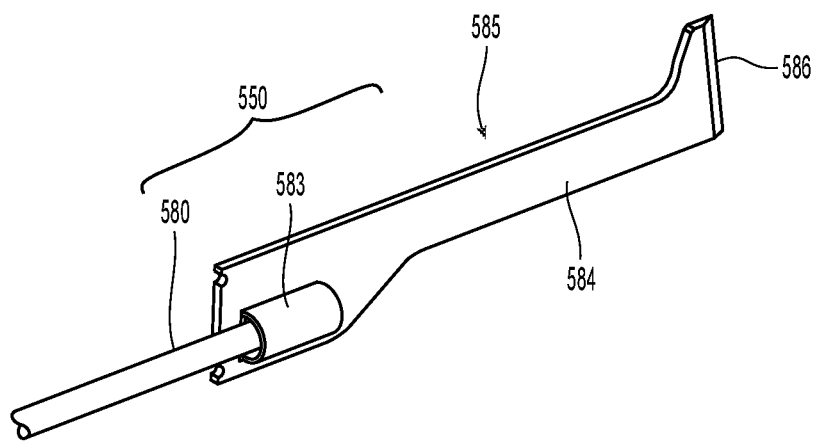
Figure 5C:
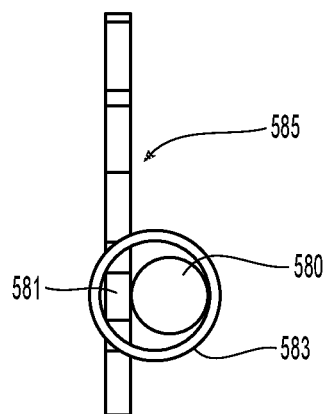

FIGS. 5A-5C show another embodiment of a knife 585 for engagement to a knife drive rod 580. More particularly, knife 585 includes a knife body 584 having a distal end 586 and a proximal end 582, the distal end 586 including a sharpened edge for cutting tissue and the proximal end 582 including an aperture 587 defined therein for capturing the knife drive rod 580. Together the knife 585 and knife drive rod 580 form a knife assembly 550. A capture tab 581 is etched from the proximal end 582 into the aperture 587 and is configured to capture and secure a tube 583 therein. The inner periphery of the tube 583 is configured to engage, e.g., threadably engage, the knife drive rod 580. During assembly, the tube 583 and the knife drive rod 580 may be spot-welded or crimped after engagement within the tube 583 to provide additional engagement of the knife drive rod 580 therein.

Since the knife drive rod 580 needs to be flexible to accommodate articulation of the jaw members 110, 120, and the knife body 584 needs to be sufficiently strong to cut through tissue on a repeated basis, the knife drive rod 580 and the knife body 584 are typically made from dissimilar materials and any such weld or bond may be weaker than desired. Thus additional mechanical engagement between the two elements, e.g., the knife drive rod 580 and knife body 584, is needed to prevent mechanical failure. Tube 583 may be made from any type of metal, e.g., stainless steel, that will provide a secure weld to knife body 584.

In embodiments, the knife body 584 and the tube 583 are made from the same material, e.g., stainless steel, to assure a good weld. The tube 583 may be dimensioned to securely seat within aperture 587 after assembly of the knife drive rod 580 within aperture 587 and about capture tab 586 to provide additional mechanical engagement between the knife body 584 and the knife drive rod 580. By providing a strong mechanical connection between the knife drive rod 580 and the tube 583 and a strong mechanical connection between the tube 583 and the knife body 584, the chances of mechanical failure are greatly reduced.

Figure 6A:
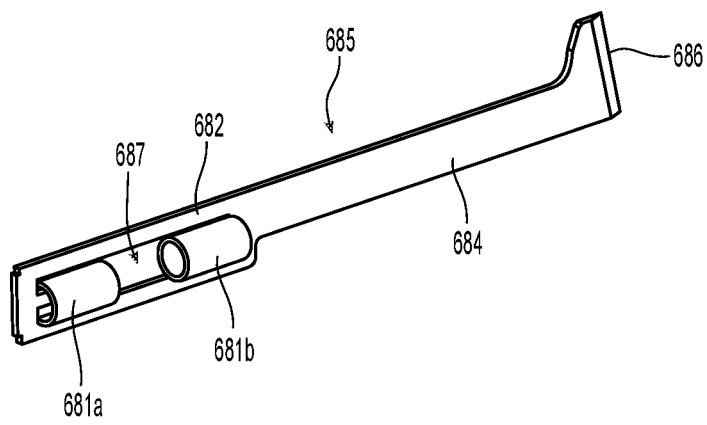
FIGS. 6A, 6B and 6C are enlarged schematic views of another embodiment of an engagement feature for coupling a knife blade to a knife drive rod exemplifying the aspects and features of the present disclosure.
Figure 6B:
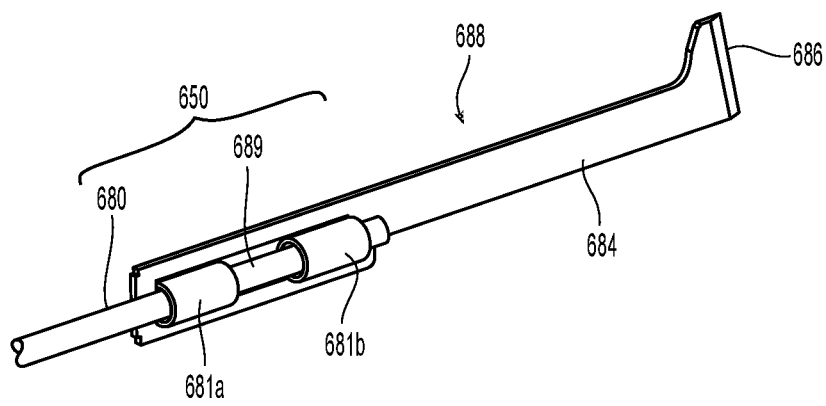
Figure 6C:
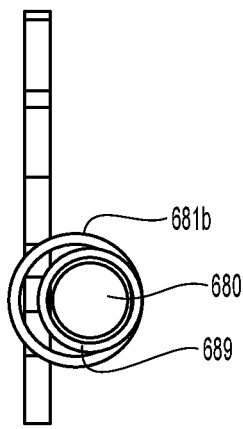

FIGS. 6A-6C show another embodiment of a knife 685 for engagement to a knife drive rod 680. More particularly, knife 685 includes a knife body 684 having a distal end 686 and a proximal end 682, the distal end 686 including a sharpened edge for cutting tissue and the proximal end 682 including an aperture 687 defined therein for capturing the knife drive rod 680. Together the knife 685 and knife drive rod 680 form a knife assembly 650. A pair of capture tubes 681a and 681b is welded (or otherwise formed) into aperture 687 of proximal end 682 and is configured to capture and secure a knife drive rod 680 therein. The inner periphery of the capture tubes 681a, 681b are configured to engage, e.g., threadably engage, the knife drive rod 680. Opposing capture tabs (not shown but see FIG. 4a—capture tabs 481a, 481b) may be utilized to mechanically capture tubes 681a, 681b.

During assembly, the knife drive rod 680 is threaded through the pair of capture tubes 681a, 681b and a second tube 689 (FIG. 6C) is spot welded to the exposed portion of the knife drive rod 680 between the pair of capture tubes 681a, 681b to secure the knife drive rod 680 in place between the two capture tubes 681a, 681b. The second tube 689 is made from the same material, e.g., Nitinol, as the knife drive rod 680 to assure a strong weld and secure mechanical engagement between the knife drive rod 680 and the capture tubes 681a, 681b of the knife body 684.

Figure 7A:
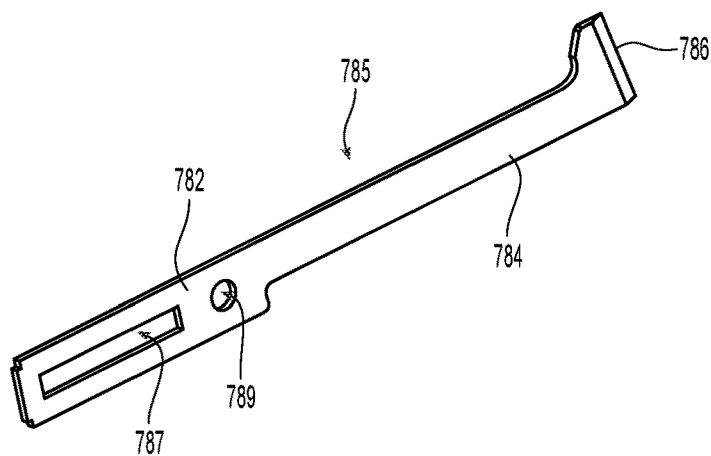
FIGS. 7A, 7B and 7C are enlarged schematic views of another embodiment of an engagement feature for coupling a knife blade to a knife drive rod exemplifying the aspects and features of the present disclosure.
Figure 7B:
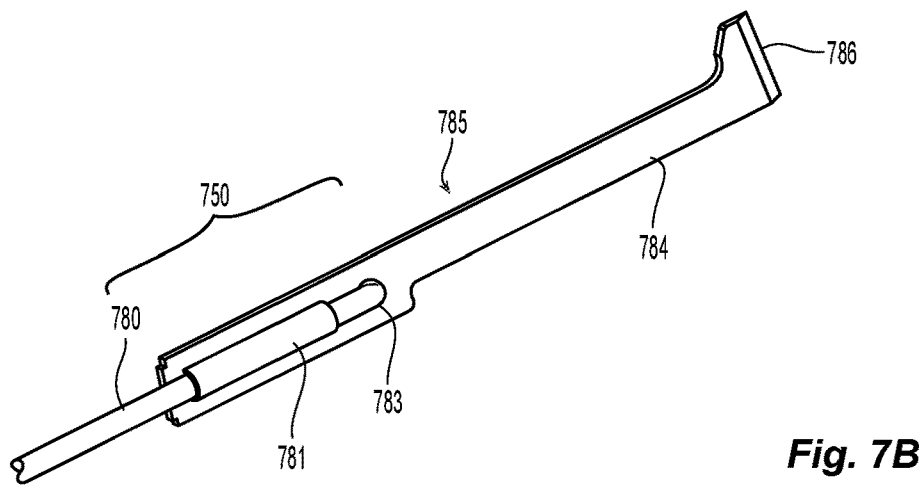
Figure 7C:
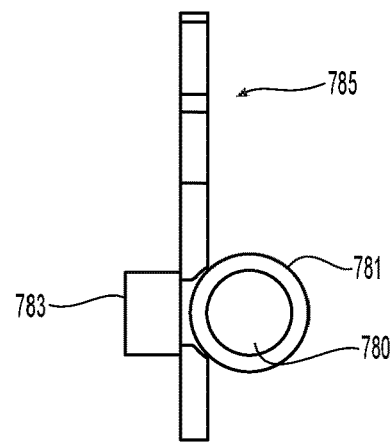

FIGS. 7A-7C show another embodiment of a knife 785 for engagement to a knife drive rod 780. More particularly, knife 785 includes a knife body 784 having a distal end 786 and a proximal end 782, the distal end 786 including a sharpened edge for cutting tissue and the proximal end 782 including a slot 787 defined therein and configured to capture a tube 781 crimped, threaded or welded onto a portion of the knife drive rod 780. Together the knife 785 and knife drive rod 780 form a knife assembly 750.

Since the knife drive rod 780 needs to be flexible to accommodate articulation of the jaw members 110, 120, and the knife body 784 needs to be sufficiently strong to cut through tissue on a repeated basis, the knife drive rod 780 and the knife body 784 are typically made from dissimilar materials and any such weld or bond may be weaker than desired. Thus additional mechanical engagement between the two elements, e.g., the knife drive rod 780 and knife body 784, is needed to prevent mechanical failure. Tube 781 may be made from any type of metal, e.g., stainless steel, that will provide a secure weld to knife body 784.

In embodiments, the knife body 784 and the tube 781 are made from the same material, e.g., stainless steel, to assure a good weld. The proximal end 782 of the knife body 780 also includes an aperture 789 defined therein configured to receive the distal end 783 of the knife drive rod 780. More particularly, the distal end 783 of the knife rod 780 is bent at an angle, e.g., 90°, such that during assembly the distal end 783 may be inserted into aperture 789 to secure the knife drive rod 780 to the knife body 784. In addition and during assembly the tube 781 is seated within slot 787 to capture the tube 781 therein and provide additional mechanical engagement between the knife drive rod 780 and the knife body 784 (See FIG. 7C).

Figure 8A:
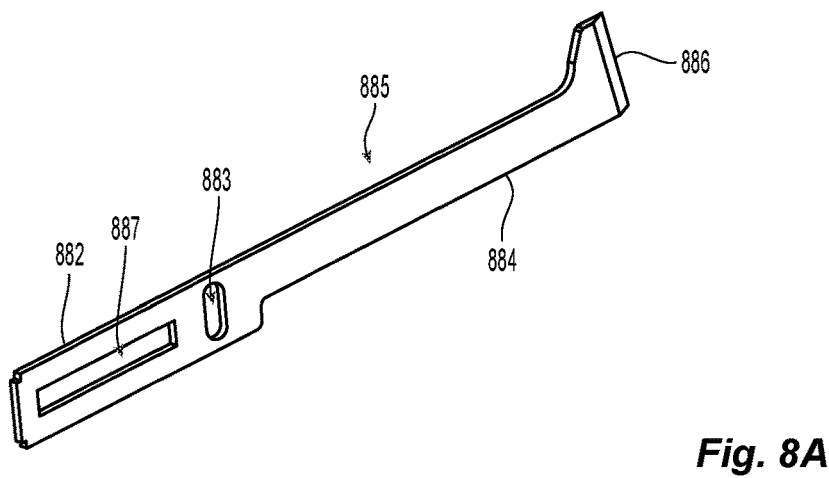
FIGS. 8A, 8B and 8C are enlarged schematic views of another embodiment of an engagement feature for coupling a knife blade to a knife drive rod exemplifying the aspects and features of the present disclosure.
Figure 8B:
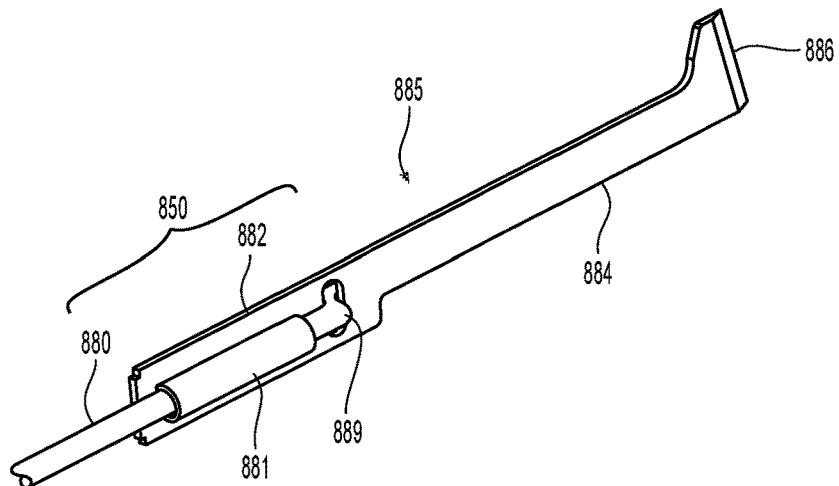
Figure 8C:
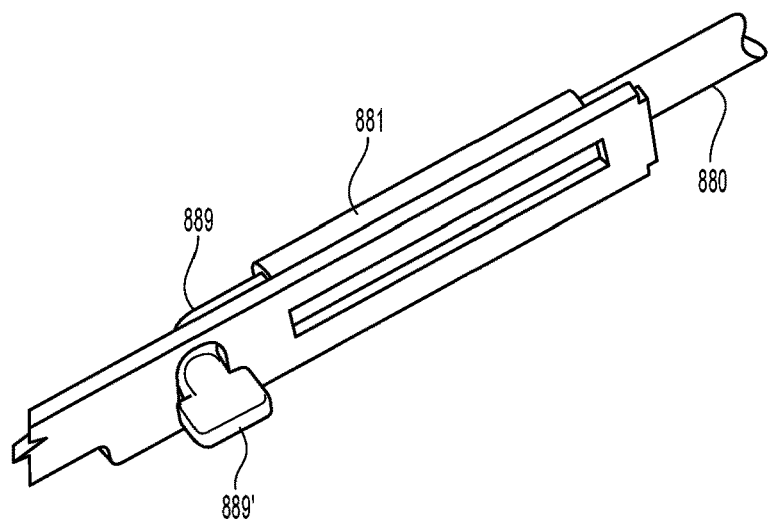

FIGS. 8A-8C show another embodiment of a knife 885 for engagement to a knife drive rod 880. More particularly, knife 885 includes a knife body 884 having a distal end 886 and a proximal end 882, the distal end 886 including a sharpened edge for cutting tissue and the proximal end 882 including a slot 887 defined therein and configured to capture a tube 881 crimped, threaded or welded onto a portion of the knife drive rod 880. Together the knife 885 and knife drive rod 880 form a knife assembly 850.

Since the knife drive rod 880 needs to be flexible to accommodate articulation of the jaw members 110, 120, and the knife body 884 needs to be sufficiently strong to cut through tissue on a repeated basis, the knife drive rod 880 and the knife body 884 are typically made from dissimilar materials and any such weld or bond may be weaker than desired. Thus additional mechanical engagement between the two elements, e.g., the knife drive rod 880 and knife body 884, is needed to prevent mechanical failure. Tube 881 may be made from any type of metal, e.g., stainless steel, that will provide a secure weld to knife body 884.

In embodiments, the knife body 884 and the tube 881 are made from the same material, e.g., stainless steel, to assure a good weld. The proximal end 882 of the knife body 880 also includes an aperture or keyway 883 defined therein configured to receive the distal end 889 of the knife drive rod 880. More particularly, the distal end 889 of the knife rod 880 is bent at an angle, e.g., 90°, such that during assembly the distal end 889 may be inserted into aperture 883 to secure the knife drive rod 880 to the knife body 884. The distal end 889 includes a locking feature 889' that is enabled once the distal end 889 is inserted into the aperture 883 during assembly.

The locking feature 889' may be a twist lock, tab lock, button snap, crimp, rivet or the like that is dimensioned to securely engage the distal end 889 within aperture 883 upon actuation, e.g., twisting, snapping, crimping, hammering, etc. thereof (FIG. 8C). In addition and during assembly the tube 881 is seated within slot 887 to capture the tube 881 therein and provide additional mechanical engagement between the knife drive rod 880 and the knife body 884 (See FIG. 8C).

Figure 9A:
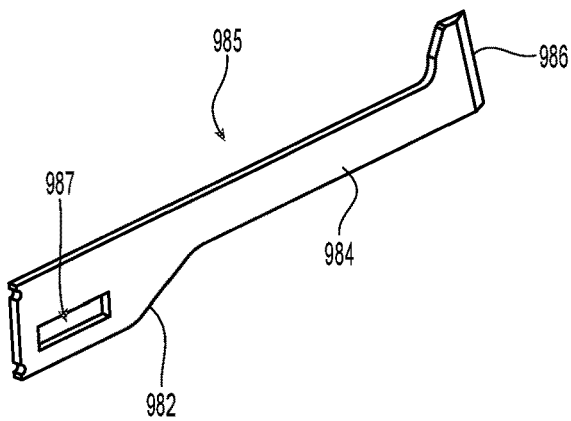
FIGS. 9A, 9B and 9C are enlarged schematic views of another embodiment of an engagement feature for coupling a knife blade to a knife drive rod exemplifying the aspects and features of the present disclosure.
Figure 9B:
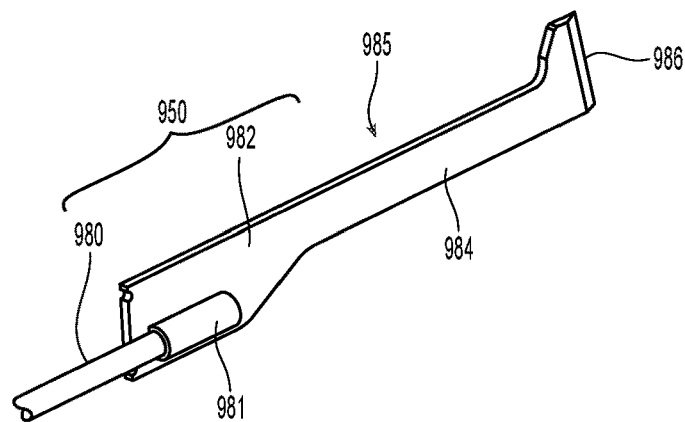

FIGS. 9A and 9B show another embodiment of a knife 985 for engagement to a knife drive rod 980. More particularly, knife 985 includes a knife body 984 having a distal end 986 and a proximal end 982, the distal end 986 including a sharpened edge for cutting tissue and the proximal end 982 including a slot 987 defined therein and configured to capture a tube 981 crimped, threaded or welded onto a portion of the knife drive rod 980. Together the knife 985 and knife drive rod 980 form a knife assembly 950.

Since the knife drive rod 980 needs to be flexible to accommodate articulation of the jaw members 110, 120, and the knife body 984 needs to be sufficiently strong to cut through tissue on a repeated basis, the knife drive rod 980 and the knife body 984 are typically made from dissimilar materials and any such weld or bond may be weaker than desired. Thus additional mechanical engagement between the two elements, e.g., the knife drive rod 980 and knife body 984, is needed to prevent mechanical failure. Tube 981, on the other hand, may be made from any type of metal, e.g., stainless steel, that will provide a secure weld to knife body 984.

In embodiments, the knife body 984 and the tube 981 are made from the same material, e.g., stainless steel, to assure a good weld. In addition and during assembly the tube 981 is seated within slot 987 to capture the tube 981 therein and provide additional mechanical engagement between the knife drive rod 980 and the knife body 984 (See FIG. 9C). As mentioned above, the knife drive rod 980 and the tube 980 are typically made from dissimilar metals, e.g., Nitinol and stainless steel, respectively, and, when welded, may produce a weaker weld.

In the particular embodiment of FIGS. 9A and 9B, if the weaker weld between the knife drive rod 980 and the tube 981 fails, the stronger bond between the knife body 984 and the tube 981 will remain intact thereby preventing the possibility of the blade 985 coming out of one or both jaw members, e.g., jaw member 120.

Figure 10:
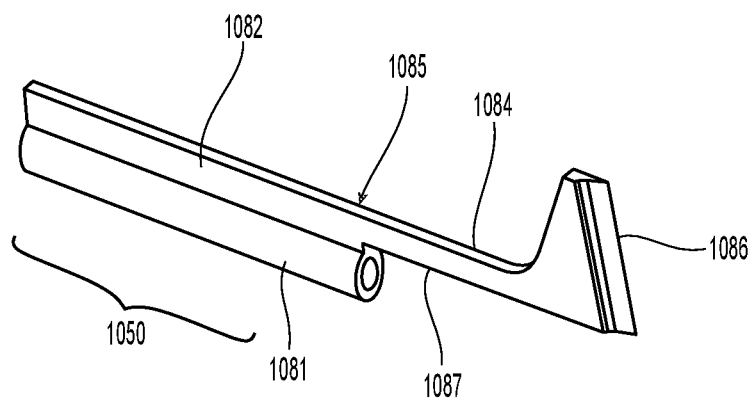
FIG. 10 is an enlarged schematic view of another embodiment of an engagement feature for coupling a knife blade to a knife drive rod exemplifying the aspects and features of the present disclosure.

FIG. 10 shows another embodiment of a knife 1085 for engagement to a knife drive rod (not shown). More particularly, knife 1085 includes a knife body 1084 having a distal end 1086 and a proximal end 1082, the distal end 1086 including a sharpened edge for cutting tissue and the proximal end 1082 configured to mechanically engage a tube 1081 which may be crimped, threaded or welded onto the proximal end 1082 along a lower edge 1087 of the knife body 1084. Together the knife 1085 and knife drive rod (not shown) form a knife assembly 1050. Tube 1081 may be made from any type of metal, e.g., stainless steel, that will provide a secure weld to knife body 1084.

In embodiments, the knife body 1084 and the tube 1081 are made from the same material, e.g., stainless steel, to assure a good weld. The knife drive rod is secured within the tube 1081 during assembly via crimping, welding or threadable engagement. Engaging the knife drive rod to the tube 1081 which is secured to the lower edge 1087 of the knife body 1084 facilitates a more balanced actuation of the knife 1085 during translation since the mechanical engagement of the knife body 1084 and the tube 1081 is along the centerline (lower edge 1087) of the knife 1085.

The present disclosure also describes various methods of engaging a knife drive rod, e.g., knife drive rod 280, 380, 480, 580, 680, 780, 880, and 980, to a respective knife, e.g., knife 285, 385, 485, 585, 685, 785, 885, 985, 1085. For example, one such method is described with reference to FIGS. 2A and 2B. The method includes: forming a knife 285 (e.g., stamping, etching, cutting, pressing, rolling (hot or cold), extruding, etc.) having proximal 282 and distal ends 286, the distal end 286 including a sharpened edge; etching (or otherwise forming) an aperture 287 within the proximal end 282 of the knife 285, the aperture 287 including a series of fins 283 disposed therein; weaving a distal end of a knife rod 280 through the series of fins 283 in an alternating manner; and engaging a cap 281 onto the distal end of the knife drive rod 280 to secure the knife drive rod 280 within the aperture 287 of the knife 285. One or more fins 283 may include a recess 283' formed therein configured to laterally secure the knife drive rod 285 within the aperture 287. The distal end of the drive rod 280 may be weaved through the fins 283 and recesses 283'. The aperture 287 may be formed within knife 285 via etching, cutting, stamping or any other method known in the art.

FIGS. 3A-3C show another method of engaging a knife drive rod 380 to a knife 385 according the present disclosure. Similar to the embodiment shown in FIGS. 2A and 2B, the method includes: forming a knife 385 having proximal 382 and distal ends 386, the distal end 386 including a sharpened edge; etching (or otherwise forming) an aperture 387 within the proximal end 382 of the knife 385, the aperture 387 including a series of fins 383 disposed therein; etching or otherwise forming a second aperture 389 within the proximal end 382 of the knife 385; weaving a distal end of a knife rod 380 through the series of fins 383 in an alternating manner; bending a distal end 381 of the knife drive rod 380; and engaging the bent distal end 381 into the second aperture 389 formed within the proximal end 382 of the knife 385 to secure the knife drive rod 380 within the aperture 387 of the knife 385.

FIGS. 4A and 4B show another method of engaging a knife drive rod 480 to a knife 485 according the present disclosure. Similar to the embodiments shown above, the method includes: forming a knife 485 having proximal 482 and distal ends 486, the distal end 486 including a sharpened edge; etching (or otherwise forming) an aperture 487 within the proximal end 482 of the knife 485, the aperture 487 including a pair of opposing capture tabs 481a, 481b disposed therein; engaging (threading, crimping or otherwise capturing) a tube 483 onto a distal end of a knife drive rod 480; engaging the tube 483 between the two opposing capture tabs 481a, 481b to seat the tube 483 within the aperture 487; and securing (welding, crimping, or otherwise) the tube 483 to the proximal end 482 of the knife 485 to secure the knife drive rod 480 and tube 483 to the knife 485.

FIGS. 5A-5C show another method of engaging a knife drive rod 580 to a knife 585 according the present disclosure. Similar to the embodiment shown above with respect to FIGS. 4A and 4B, the method includes: forming a knife 585 having proximal 582 and distal ends 586, the distal end 586 including a sharpened edge; etching (or otherwise forming) an aperture 587 within the proximal end 582 of the knife 585, the aperture 587 including a capture tab 581 disposed therein; engaging (threading, crimping or otherwise capturing) a tube 583 onto a distal end of a knife drive rod 580; engaging the tube 583 to the capture tab 581 to seat the tube 583 within the aperture 587; and securing (welding, crimping, or otherwise) the tube 583 to the proximal end 582 of the knife 585 to secure the knife drive rod 580 and tube 583 to the knife 585.

FIGS. 6A-6C show another method of engaging a knife drive rod 680 to a knife 685 according the present disclosure. The method includes: forming a knife 685 having proximal 682 and distal ends 686, the distal end 686 including a sharpened edge; etching (or otherwise forming) an aperture 687 within the proximal end 682 of the knife 685; engaging (e.g., welding) a pair of opposing tubes 681a, 681b within the aperture 687; feeding the knife drive rod 680 through the pair of tubes 681a, 681b; and engaging (e.g., welding or crimping) a second tube 689 to the exposed portion of the knife drive rod 680 between the pair of tubes 681a, 681b to secure the knife drive rod 680 in place between the tubes 681a, 681b. Knife drive rod 680 and the second tube 689 may be made from the same material to provide a strong weld. The knife drive rod 680 may also be threaded through the pair of tubes 681a, 681b to enhance the mechanical connection. The tubes 681a, 681b may be made from the same material as the knife 685 to enhance the weld and provide additional strength, stiffness, and/or durability.

FIGS. 7A-7C show another method of engaging a knife drive rod 780 to a knife 785 according the present disclosure. Similar to the embodiments shown above with respect to FIGS. 4A and 4B and FIGS. 3A-3C, the method includes: forming a knife 785 having proximal 782 and distal ends 786, the distal end 786 including a sharpened edge; etching (or otherwise forming) an aperture 787 within the proximal end 782 of the knife 785; etching or otherwise forming a second aperture 789 within the proximal end 782 of the knife 785; engaging (threading, crimping or otherwise capturing) a tube 781 onto a distal end 783 of a knife drive rod 780; bending the distal end 783 of the knife drive rod 780; seating the tube 781 within the aperture 787; and engaging the bent distal end 783 into the second aperture 789 formed within the proximal end 782 of the knife 785 to secure the tube 781 within the aperture 787 of the knife 785 and secure the bent distal end 783 to the proximal end 782 of the knife 785.

FIGS. 8A-8C show another method of engaging a knife drive rod 880 to a knife 885 according the present disclosure. Similar to the embodiments shown above with respect to FIGS. 7A-7C, the method includes: forming a knife 885 having proximal 882 and distal ends 886, the distal end 886 including a sharpened edge; etching (or otherwise forming) an aperture 887 within the proximal end 882 of the knife 885; etching or otherwise forming a slot 883 within the proximal end 882 of the knife 885; engaging (threading, crimping or otherwise capturing) a tube 881 onto a distal end 889 of a knife drive rod 880; bending the distal end 889 of the knife drive rod 880; seating the tube 881 within the aperture 887; engaging the bent distal end 889 into the slot 883 formed within the proximal end 882 of the knife 885; actuating a locking feature 889' (e.g., twist lock, tab lock, button snap, crimp, rivet or the like) to engage and secure (via twisting, snapping, crimping, hammering, etc.) the distal end 889 within the slot 883 and secure the tube 881 within the aperture 887 of the knife 885.

Figure 9C:
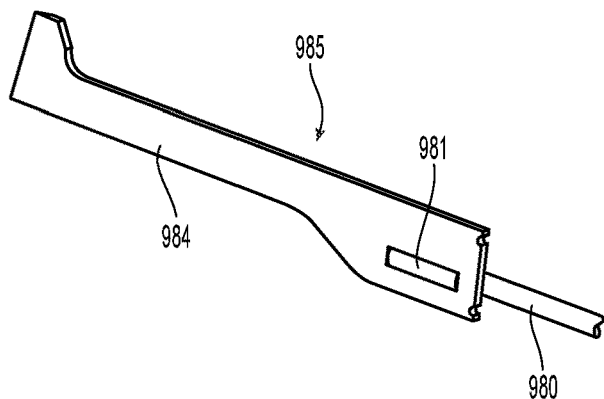

FIGS. 9A-9C show another method of engaging a knife drive rod 980 to a knife 985 according the present disclosure. Similar to many of the above-described embodiments shown above with respect to the various figures, the method includes: forming a knife 985 having proximal 982 and distal ends 986, the distal end 986 including a sharpened edge; etching (or otherwise forming) an aperture 987 within the proximal end 982 of the knife 985; engaging (threading, crimping or otherwise capturing) a tube 981 onto a distal end of a knife drive rod 980; seating the tube 981 within the aperture 987; and securing the tube 981 within the aperture 987 via welding, crimping, etc. As mentioned above, the knife body 984 and the tube 981 are made from the same material, e.g., stainless steel, to assure a good weld.

In addition and during assembly the tube 981 is seated within slot 987 to capture the tube 981 therein and provide additional mechanical engagement between the knife drive rod 980 and the knife body 984 (See FIG. 9C). As mentioned above, the knife drive rod 980 and the tube 980 are typically made from dissimilar metals, e.g., Nitinol and stainless steel, respectively, and, when welded, may produce a weaker weld. If the weaker weld between the knife drive rod 980 and the tube 981 fails, the stronger bond between the knife body 984 and the tube 981 will remain intact thereby preventing the possibility of the blade 985 coming out of one or both jaw members, e.g., jaw member 120.

FIG. 10 shows another method of engaging a knife drive rod 1080 to a knife 1085 according the present disclosure.

The method includes forming a knife 1085 having proximal 1082 and distal ends 1086, the distal end 1086 including a sharpened edge; engaging (e.g., welding or other mechanical attachment) a tube 1081 to a lower edge 1087 of the knife 1085; and engaging (threading, crimping or otherwise capturing) a distal end of a knife drive rod (not shown) within the tube 1081. Tube 1081 may be made from any type of metal, e.g., stainless steel, that will provide a secure weld to knife body 1084 (which is also made from a similar material, e.g., stainless steel) to assure a good weld.

Engaging the knife drive rod to the tube 1081 (which is secured to the lower edge 1087 of the knife body 1084) facilitates a more balanced actuation of the knife 1085 during translation since the mechanical engagement of the knife body 1084 and the tube 1081 is along the centerline (lower edge 1087) of the knife 1085.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. For example, the knife body and tube do not necessarily have to be made from the exact same materials. Similar materials, or any two materials that can be welded together to allow for a durable weld joint could be used.

What is claimed is:

1. A surgical instrument, comprising:
    an end effector assembly; and
    a knife assembly, comprising:
        a knife extending along a longitudinal knife axis, the knife including a knife body having a lateral side, a distal end portion including a sharpened edge, and a proximal end portion defining an aperture;
        a tube at least partially disposed within the aperture of the knife, the tube having an outer surface secured to the lateral side of the knife body, the tube defining a longitudinal tube axis that is offset relative to the longitudinal knife axis; and
        a knife drive rod disposed within the tube to secure the knife drive rod to the tube, the knife drive rod extending proximally beyond the tube and the knife, wherein the knife drive rod is configured to move the knife through the end effector assembly for cutting tissue.

2. The surgical instrument according to claim 1, wherein the knife drive rod defines a longitudinal rod axis that is offset relative to the longitudinal knife axis.

3. The surgical instrument according to claim 1, wherein the longitudinal tube axis is laterally offset relative to the longitudinal knife axis.

4. The surgical instrument according to claim 1, wherein a proximal end of the knife extends proximal to a proximal end of the tube.

5. A surgical instrument, comprising:
    an end effector assembly; and
    a knife assembly, comprising:
        a knife defining a longitudinal knife axis, wherein a proximal end portion of the knife defines an aperture;
        a tube at least partially disposed within the aperture, the tube having an outer surface attached to a lateral side of the knife, the tube defining a longitudinal tube axis that is offset relative to the longitudinal knife axis; and
        a knife drive rod disposed within the tube and extending proximally beyond a proximal-most end of the tube and a proximal-most end of the knife, the knife drive rod configured to move the knife through the end effector assembly for cutting tissue.

6. The surgical instrument according to claim 5, wherein the knife drive rod defines a longitudinal rod axis that is offset relative to the longitudinal knife axis.

7. The surgical instrument according to claim 5, wherein the longitudinal tube axis is laterally offset relative to the longitudinal knife axis.

8. A surgical instrument, comprising:
    an end effector assembly; and
    a knife assembly, comprising:
        a knife defining a longitudinal knife axis, wherein a proximal end portion of the knife defines an aperture;

a tube at least partially disposed within the aperture, the tube having an outer surface attached to a lateral side of the knife, the tube defining a longitudinal tube axis that is offset relative to the longitudinal knife axis; and a knife drive rod directly coupled to an inner surface of the tube and configured to move the knife through the end effector assembly for cutting tissue.

9. The surgical instrument according to claim 8, wherein the knife drive rod defines a longitudinal rod axis that is offset relative to the longitudinal knife axis.

10. The surgical instrument according to claim 8, wherein the longitudinal tube axis is laterally offset relative to the longitudinal knife axis.

\* \* \* \* \*